US007247619B2

(12) United States Patent
Kirkegaard et al.

(10) Patent No.: US 7,247,619 B2
(45) Date of Patent: Jul. 24, 2007

(54) VIRAL VECTORS USEFUL IN INDUCTION OF HUMORAL OR CELLULAR IMMUNITY

(76) Inventors: Karla Kirkegaard, 830 Hamilton Ave., Palo Alto, CA (US) 94301; Dana A. Dodd, 3153 Stelling Dr., Palo Alto, CA (US) 94303; Stephen B. Deitz, 3364 Toomer Kiln Cir., Mount Pleasant, SC (US) 29466; John Doedens, 119 NW. 50th St., Seattle, WA (US) 98107

( * ) Notice: Subject to any disclaimer, the term of this patent is extended or adjusted under 35 U.S.C. 154(b) by 376 days.

(21) Appl. No.: 10/276,752

(22) PCT Filed: May 18, 2001

(86) PCT No.: PCT/US01/16000

§ 371 (c)(1),
(2), (4) Date: Sep. 2, 2003

(87) PCT Pub. No.: WO01/90384

PCT Pub. Date: Nov. 29, 2001

(65) Prior Publication Data

US 2004/0052765 A1 Mar. 18, 2004

Related U.S. Application Data

(60) Provisional application No. 60/205,522, filed on May 19, 2000.

(51) Int. Cl.
*A61K 48/00* (2006.01)
*C12N 15/74* (2006.01)

(52) U.S. Cl. ...................... 514/44; 435/320.1; 435/455

(58) Field of Classification Search ..................... None
See application file for complete search history.

(56) References Cited

U.S. PATENT DOCUMENTS

| | | | |
|---|---|---|---|
| 5,622,705 | A | 4/1997 | Morrow |
| 6,015,694 | A | 1/2000 | Dubensky et al. |
| 6,589,531 | B1 | 7/2003 | Andino-Pavlovsky et al. |
| 6,680,169 | B2 | 1/2004 | Morrow et al. |
| 6,866,853 | B2 | 3/2005 | Egorov et al. |
| 6,893,643 | B2 | 5/2005 | Andino-Pavlovsky et al. |

OTHER PUBLICATIONS

Choe et al, Virol 2005; 18-29.*
Doedens et al, J Virol 1997;71:9054-64.*
Crotty et al, J Virol 1999;73:9485-95.*
Deonarain, 1998, Expert Opin. Ther. Pat., vol. 8, pp. 53-69.*
Miller et al, 1995, FASEB J., vol. 9, pp. 190-199.*
Makrides et al, Protein Exp Pur 1999;17:183-202.*
Zink et al, Gene Ther Mol Biol Jan. 2001;6:1-24.*
French Anderson, Hum Gene Ther 2002;13:1261-2.*
Weiss, Washington Post Mar. 2005.*
Hewson, "RNA Viruses: Emerging Vectors for Vaccination and Gene Therapy," (2000) Mole. Med. Today 6:28-35.

Aldabe et al., "Induction of Membrane Profileration by Poliovirus Proteins 2C and 2BC," (1995) Biochem. Biophys. Res. Commun. 206:64-76.

Bienz et al., "Association of Polioviral Proteins of the P2 Genomic Region with the Viral Replication Complex and Virus-Induced Membrane Synthesis as Visualized by Electron Microscopic Immunocytochemistry and Autoradiography," (1987) Virology 160:220-226.

Cho et al., Membrane Rearrangement and Vesicle Induction by Recombinant Poliovirus 2C and 2BC in Human Cells, (1994) Virology 202:129-145.

Dales et al., "Electron Microscopic Study of the Formation of Poliovirus," (1965) Virology 26:379-389.

Doedens et al., "Inhibition of Cellular Protein Secretion by Poliovirus Proteins 2B and 3A," (1995) Embo J. 14:894-907.

Bienz et al., "Structural and Functional Characterization of the Poliovirus Replication Complex," (1992) J. Virology 66:2740-2747.

Bienz et al., "Characteristics of the Poliovirus Replication Complex," (1994) Arch. Virol. Suppl. 9:147-157.

Bernstein et al., "Poliovirus Mutant that Contains a Cold-Sensitive Defect in Viral RNA Synthesis," (1988) J. Virol. 62:2922-2928.

Andino et al., "Engineering Poliovirus as a Vaccine Vector for the Expression of Diverse Antigens," (1994) Science 265:1448-1451.

Burke et al., "Antigen Chimaeras of Poliovirus as Potential New Vaccines," (1988) Nature 332:81-82.

Mattion et al., "Attenuated Poliovirus Strain as a Live Vector: Expression of Regions of Rotavirus Outer Capsid Protein VP7 by Using Recombinant Sabin 3 Viruses," (1994) J. Virol. 68:3925-3933.

Ansardi et al., Characterization of Poliovirus Replicons Encoding Carcinoembryonic Antigen (1994) 54:6359-6364.

Dietz S.B. et al., "MHC I-Dependent Antigen Presentation is Inhibited by Polivirus Protein, 3a", Proc. Natl. Acad. Sci., Dec. 2000, (97) No. 25 pp. 13790-13795.

(Continued)

*Primary Examiner*—Q. Janice Li
(74) *Attorney, Agent, or Firm*—Bozicevic, Field & Francis LLP; Carol L. Francis

(57) ABSTRACT

The invention features recombinant viral vectors that take advantage of the activity of picornaviral protein 3A in modulating cytokine secretion and antigen presentation on MHC Class I (MHC I), which in turn provides for modulation of a Th1-mediated immune response to the transfected host cell. Specifically, a recombinant viral vector comprising a sequence encoding picornaviral protein 3A provides for decreased antigen presentation on MHC I and a decreased incidence of Th1-mediated immune response, while a recombinant picornaviral vector that is deficient in protein 3A production provides for increased cytokine secretion, increased antigen presentation on MHC I and increased Th1-mediated immune response towards the transfected host cell. The invention also features methods of inducing humoral or cellular immunity using the vectors.

16 Claims, 6 Drawing Sheets

OTHER PUBLICATIONS

Figure 1:
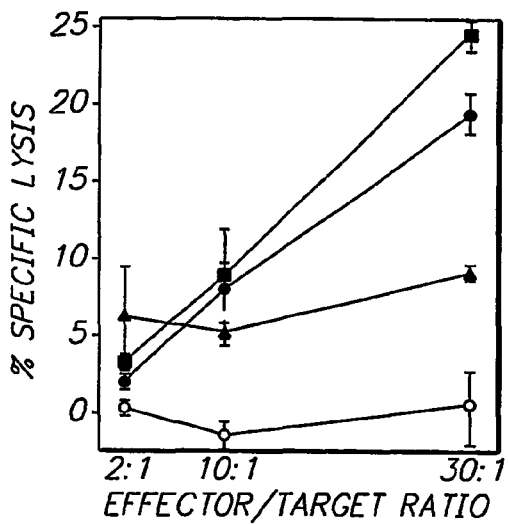
Figure 3A:
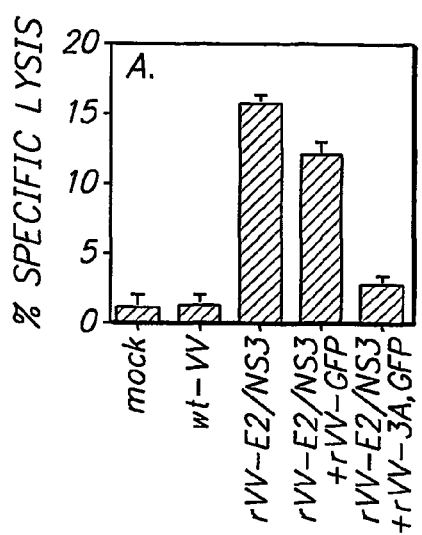
Figure 3B:
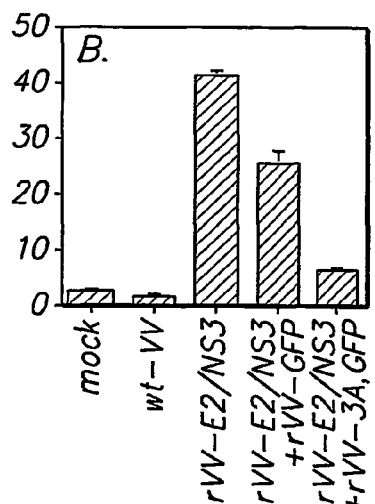
Figure 3C:
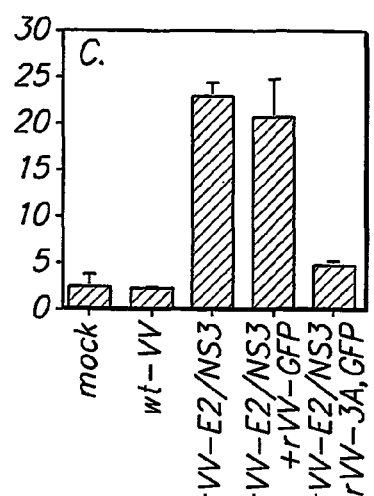

Gern, J.E. et al. Rhinovirus Inhibits Antigen-Specific T Cell Proliferation Through an Intercellular Adhesion Molecule-1-Dependant Mechanism. J. Infect. Dis. 1996, (174), pp. 1143-1150.

Louis Alexander et al. "Polioviruses Containing Picornavirus Type 1 and/or Type 2 Internal Ribosomal Entry Site Elements: Genetic Hybrids and the Expression of a Foreign Gene", Pro. Nat. Acad. Sci. USA vol. 91, pp. 1406-1410 (Feb. 1994).

John R. Doedens et al. "Inhibition of Endoplasmic Reticulum-to-Golgi Traffic by Poliovirus Protein 3A: Genetic and Ultrastructural Analysis", Journal of Virology, vol. 7, No. 12, pp. 9054-9064, (Dec. 1997).

Stefanie Mandl et al. "Polivirus Vaccine Vectors Elicit Antigen-Specific Cytotoxic T Cells and Protect Mice Against Lethal Challenge with Malignant Melanoma Cells Expressing a Model Antigen", Proc. Natl. Acad. Sci. USA vol. 95, pp. 8216-8221 (Jul. 1998).

Pak Phi Poon et al. "Retrograde Transport from the Yeast Golgi is Medicated by two ARF GAP Proteins With Overlapping Function", The Embo Journal vol. 18, No. 3, pp. 555-564 (1999).

Andreas Schlegel et al. "Cellular Origin and Ultrastructure of Membranes Induced During Poliovirus Infection", Journal of Virology, vol. 70, No. 10, pp. 6576-6588 (Oct. 1996).

* cited by examiner

```
POLIO_1    GPLQYK---DLKIDIKTS-PPPECINDLLQAVDSQEVRDYCE-KKGWIV-NITSQVQTERNINRAMTILQAVTTFAAVAGVVYVMYKLFAGHQ
POLIO_3A2  GPLQYK---DLKIDIKTSSPPPECINDLLQAVDSQEVRDYCE-KKGWIV-NITSQVQTERNINRAMTILQAVTTFAAVAGVVYVMYKLFAGHQ
COX_B3     GPPVYR---EIKISVAPETPPPPAIADLLKSVDSEAVREYCK-EKGWLVPEINSTLQIEKHVSRAFICLQALTTFVSVAGIIYIIYKLFAGFQ
HRV_14     GP-VYK---DLEIDVCNT-PPSECINDLLKSVDSEEIREYCK-KKKWII--PEIPTNIERAMNQASMIINTILMFVSTLGIVYVIYKLFAQTQ
HRV_16     GP-----------ISMDKPPPPAITDLLRSVRTPEVIKYCQ-DNKWIVP---ADCQIERDLNIANSITIIANIISIAGIIYIIYKLFCSLQ
HRV_2      GP-----------IDMKNPPPPPAITDLLQSVRTPEVIKYCE-GNRWIIP---AECKIEKELNLANTIITIIANVIGMARIIYVIYKLFCTLQ
EMCV       GPVDEVSFHSVVQQLKARQQATDEQLEELQEA-FAKVQERNSVFSDWLK----ISAML-CAATLALSQVVKMAKAVKQMVKPDLVRVQLDEQEQ
TH_BeAn    SPPDWEHFENILTCLRQNNAALQDQLDELQEA-FAQARERSDFLSDWLK---VSAII-FAGIASLSAVIKLASKFKESIWPTPVRVELSEGEQ
TH_GDVII   SPPDWQHFENILTCLRQNNAALQDQVDELQEA-FTQARERSDFLSDWLK---VSAII-FAGIVSLSAVIKLASKFKESIWPTPVRVELSEGEQ
HAV_HM175  GISDDDN-DSAVAEFFQSFPSGEPSNSKLSGF-FQSVT--N---HKWVA----VGAAVGILGVLVGGWFVYKHFSRKEE-EP---IPAE----
HAV_FG     GISDNN---AVAEFFQSFPSGEPSNSKLSGF-FQSVT--N---HKWVA----VGAAVGILGVLVGGWFVYRHFSRHEE-EP---IPAE----
```

FIG. 7

SEQUENCE LISTING

<160> NUMBER OF SEQ ID NOS: 11

<210> SEQ ID NO 1
<211> LENGTH: 87
<212> TYPE: PRT
<213> ORGANISM: human poliovirus type 1

<400> SEQUENCE: 1

Gly Pro Leu Gln Tyr Lys Asp Leu Lys Ile Asp Ile Lys Thr Ser Pro

```
                1               5                  10                 15
Pro Pro Glu Cys Ile Asn Asp Leu Leu Gln Ala Val Asp Ser Gln Glu
                20                  25                 30

Val Arg Asp Tyr Cys Glu Lys Lys Gly Trp Ile Val Asn Ile Thr Ser
                35                  40                 45

Gln Val Gln Thr Glu Arg Asn Ile Asn Arg Ala Met Thr Ile Leu Gln
                50                  55                 60

Ala Val Thr Ile Phe Ala Val Ala Gly Val Val Tyr Val Met Tyr
 65                 70                  75                 80

Lys Leu Phe Ala Gly His Gln
                85

<210> SEQ ID NO 2
<211> LENGTH: 88
<212> TYPE: PRT
<213> ORGANISM: Artificial Sequence
<220> FEATURE:
<223> OTHER INFORMATION: variant 3A protein

<400> SEQUENCE: 2

Gly Pro Leu Gln Tyr Lys Asp Leu Lys Ile Asp Ile Lys Thr Ser Ser
 1               5                  10                 15

Pro Pro Glu Cys Ile Asn Asp Leu Leu Gln Ala Val Asp Ser Gln
                20                  25                 30

Glu Val Arg Asp Tyr Cys Glu Lys Lys Gly Trp Ile Val Asn Ile Thr
                35                  40                 45

Ser Gln Val Gln Thr Glu Arg Asn Ile Asn Arg Ala Met Thr Ile Leu
                50                  55                 60

Gln Ala Val Thr Ile Phe Ala Ala Val Ala Gly Val Val Tyr Val Met
 65                 70                  75                 80

Tyr Lys Leu Phe Ala Gly His Gln
                85

<210> SEQ ID NO 3
<211> LENGTH: 89
<212> TYPE: PRT
<213> ORGANISM: coxsackievirus

<400> SEQUENCE: 3

Gly Pro Pro Val Tyr Arg Glu Ile Lys Ile Ser Val Ala Pro Glu Thr
 1               5                  10                 15

Pro Pro Pro Pro Ala Ile Ala Asp Leu Leu Lys Ser Val Asp Ser Glu
                20                  25                 30

Ala Val Arg Glu Tyr Cys Lys Glu Lys Gly Trp Leu Val Pro Glu Ile
                35                  40                 45

Asn Ser Thr Leu Gln Ile Glu Lys His Val Ser Arg Ala Phe Ile Cys
                50                  55                 60

Leu Gln Ala Leu Thr Ile Phe Val Ser Val Ala Gly Ile Ile Tyr Ile
 65                 70                  75                 80

Ile Tyr Lys Leu Phe Ala Gly Phe Gln
                85

<210> SEQ ID NO 4
<211> LENGTH: 85
<212> TYPE: PRT
<213> ORGANISM: human rhinovirus

<400> SEQUENCE: 4
```

-continued

```
Gly Pro Val Tyr Lys Asp Leu Glu Ile Asp Val Cys Asn Thr Pro Pro
1               5                   10                  15

Ser Glu Cys Ile Asn Asp Leu Leu Lys Ser Val Asp Ser Glu Ile
            20                  25                  30

Arg Glu Tyr Cys Lys Lys Lys Trp Ile Ile Pro Glu Ile Pro Thr
            35                  40                  45

Asn Ile Glu Arg Ala Met Asn Gln Ala Ser Met Ile Ile Asn Thr Ile
50                      55                  60

Leu Met Phe Val Ser Thr Leu Gly Ile Val Tyr Val Ile Tyr Lys Leu
65                      70                  75                  80

Phe Ala Gln Thr Gln
                85
```

<210> SEQ ID NO 5
<211> LENGTH: 77
<212> TYPE: PRT
<213> ORGANISM: human rhinovirus

<400> SEQUENCE: 5

```
Gly Pro Ile Ser Met Asp Lys Pro Pro Pro Ala Ile Thr Asp Leu
1               5                   10                  15

Leu Arg Ser Val Arg Thr Pro Glu Val Ile Lys Tyr Cys Gln Asp Asn
            20                  25                  30

Lys Trp Ile Val Pro Ala Asp Cys Gln Ile Glu Arg Asp Leu Asn Ile
            35                  40                  45

Ala Asn Ser Ile Ile Thr Ile Ile Ala Asn Ile Ile Ser Ile Ala Gly
            50                  55                  60

Ile Ile Tyr Ile Ile Tyr Lys Leu Phe Cys Ser Leu Gln
65                      70                  75
```

<210> SEQ ID NO 6
<211> LENGTH: 77
<212> TYPE: PRT
<213> ORGANISM: human rhinovirus

<400> SEQUENCE: 6

```
Gly Pro Ile Asp Met Lys Asn Pro Pro Pro Ala Ile Thr Asp Leu
1               5                   10                  15

Leu Gln Ser Val Arg Thr Pro Glu Val Ile Lys Tyr Cys Glu Gly Asn
            20                  25                  30

Arg Trp Ile Ile Pro Ala Glu Cys Lys Ile Glu Lys Glu Leu Asn Leu
            35                  40                  45

Ala Asn Thr Ile Ile Thr Ile Ile Ala Asn Val Ile Gly Met Ala Arg
            50                  55                  60

Ile Ile Tyr Val Ile Tyr Lys Leu Phe Cys Thr Leu Gln
65                      70                  75
```

<210> SEQ ID NO 7
<211> LENGTH: 88
<212> TYPE: PRT
<213> ORGANISM: encephalomyocarditis virus

<400> SEQUENCE: 7

```
Gly Pro Val Asp Glu Val Ser Phe His Ser Val Gln Gln Leu Lys
1               5                   10                  15

Ala Arg Gln Gln Ala Thr Asp Glu Gln Leu Glu Glu Leu Gln Glu Ala
            20                  25                  30

Phe Ala Lys Val Gln Glu Arg Asn Ser Val Phe Ser Asp Trp Leu Lys
```

-continued

```
        35                  40                  45

Ile Ser Ala Met Leu Cys Ala Ala Thr Leu Ala Leu Ser Gln Val Val
    50                  55                  60

Lys Met Ala Lys Ala Val Lys Gln Met Val Lys Pro Asp Leu Val Arg
65                  70                  75                  80

Val Gln Leu Asp Glu Gln Glu Gln
                85

<210> SEQ ID NO 8
<211> LENGTH: 88
<212> TYPE: PRT
<213> ORGANISM: Theiler's virus

<400> SEQUENCE: 8

Ser Pro Pro Asp Trp Glu His Phe Glu Asn Ile Leu Thr Cys Leu Arg
 1               5                  10                  15

Gln Asn Asn Ala Ala Leu Gln Asp Gln Leu Asp Glu Leu Gln Glu Ala
            20                  25                  30

Phe Ala Gln Ala Arg Glu Arg Ser Asp Phe Leu Ser Asp Trp Leu Lys
        35                  40                  45

Val Ser Ala Ile Ile Phe Ala Gly Ile Ala Ser Leu Ser Ala Val Ile
    50                  55                  60

Lys Leu Ala Ser Lys Phe Lys Glu Ser Ile Trp Pro Thr Pro Val Arg
65                  70                  75                  80

Val Glu Leu Ser Glu Gly Glu Gln
                85

<210> SEQ ID NO 9
<211> LENGTH: 88
<212> TYPE: PRT
<213> ORGANISM: Theiler's virus

<400> SEQUENCE: 9

Ser Pro Pro Asp Trp Gln His Phe Glu Asn Ile Leu Thr Cys Leu Arg
 1               5                  10                  15

Gln Asn Asn Ala Ala Leu Gln Asp Gln Val Asp Glu Leu Gln Glu Ala
            20                  25                  30

Phe Thr Gln Ala Arg Glu Arg Ser Asp Phe Leu Ser Asp Trp Leu Lys
        35                  40                  45

Val Ser Ala Ile Ile Phe Ala Gly Ile Val Ser Leu Ser Ala Val Ile
    50                  55                  60

Lys Leu Ala Ser Lys Phe Lys Glu Ser Ile Trp Pro Ile Pro Val Arg
65                  70                  75                  80

Val Glu Leu Ser Glu Gly Glu Gln
                85

<210> SEQ ID NO 10
<211> LENGTH: 74
<212> TYPE: PRT
<213> ORGANISM: hepatitis A virus

<400> SEQUENCE: 10

Gly Ile Ser Asp Asp Asp Asn Asp Ser Ala Val Ala Glu Phe Phe Gln
 1               5                  10                  15

Ser Phe Pro Ser Gly Glu Pro Ser Asn Ser Lys Leu Ser Gly Phe Phe
            20                  25                  30

Gln Ser Val Thr Asn His Lys Trp Val Ala Val Gly Ala Ala Val Gly
        35                  40                  45
```

```
Ile Leu Gly Val Leu Val Gly Gly Trp Phe Val Tyr Lys His Phe Ser
    50                  55                  60

Arg Lys Glu Glu Glu Pro Ile Pro Ala Glu
65                  70

<210> SEQ ID NO 11
<211> LENGTH: 71
<212> TYPE: PRT
<213> ORGANISM: hepatitis A virus

<400> SEQUENCE: 11

Gly Ile Ser Asp Asn Ala Val Ala Glu Phe Phe Gln Ser Phe Pro
1               5                   10                  15

Ser Gly Glu Pro Ser Asn Ser Lys Leu Ser Gly Phe Phe Gln Ser Val
                20                  25                  30

Thr Asn His Lys Trp Val Ala Val Gly Ala Ala Val Gly Ile Leu Gly
            35                  40                  45

Val Leu Val Gly Gly Trp Phe Val Tyr Arg His Phe Ser Arg His Glu
    50                  55                  60

Glu Glu Pro Ile Pro Ala Glu
65                  70
```

VIRAL VECTORS USEFUL IN INDUCTION OF HUMORAL OR CELLULAR IMMUNITY

CROSS-REFERENCE TO RELATED APPLICATIONS

This application is the National Stage of International Application No. PCT/US01/16000, filed May 18, 2001, which application claims priority benefit of U.S. application Ser. No. 60/205,522, filed, May 19, 2000.

GOVERNMENT RIGHTS

This invention was made with government support under grant no. AI25166 from the National Institutes of Health. The United States Government may have certain rights in this invention.

FIELD OF THE INVENTION

The invention relates to modulation of inflammation and the killing of infected cells by the immune system associated with vaccination and other modalities that involve delivery and expression of nucleic acid in a host.

BACKGROUND OF THE INVENTION

Nucleic acid-based therapies useful in vaccination and in delivery of polypeptides and gene replacement have made great advancements in recent years (for a brief review, see, e.g., Hewson (2000) *Mol. Med Today* 6:28–35). However the search for vehicles that provide for efficient delivery and expression of a sequence of interest without inducing undesirable side effects continues. One particular problem in this context has been in the use of viral vectors. Viral vectors exploit the natural ability of viruses to delivery genetic material to cells and use the host cell machinery to provide for expression of the encoded gene product and/or incorporation of the sequence into the host genome (as either a integrated or episomal entity). However, the transfer of the therapeutic recombinant gene to host cells not only results in expression of the gene product of interest, but may also result in the synthesis of viral proteins. Cells that express these viral proteins are recognized and killed by cytotoxic T lymphocytes, which in turn eradicate the transduced cells, promote release of cytokines, and mediate inflammation through release of cytokines. Other vectors that provide for expression of the encoded gene products in the cytoplasm of the host cell meet with the same or similar problems.

Vectors based upon picornaviral genomes have been of interest due to the widespread success of live vaccines in the now nearly world-wide eradication of poliovirus. Picornaviruses are extremely prevalent and successful viruses, replicating abundantly in organisms ranging from insects to humans. Picornaviruses include polioviruses, rhinoviruses, coxsackieviruses, and echoviruses. Picornaviruses are non-enveloped viruses that encode no known glycosylated or transmembrane proteins. However, poliovirus, the most extensively studied picornavirus, encodes at least three non-structural proteins that drastically affect host intracellular membrane structure and function. Specifically, poliovirus protein 2C induces membrane vesiculation while proteins 2B and 3A are each sufficient to inhibit protein traffic through the host secretory pathway (Aldabe et al. (1995) *Biochem. Biophys. Res. Commun.* 206:64–76; Bienz et al. (1987) *Virology* 160:220–226; Cho et al. (1994) *Virology* 202:129–145, Dales et al. (19 *Virology* 26: 379–389; Doedens et al. (1995) *Embo J* 14:894–907; Doedens et al. (1997) *J. Virol.* 71:9054–9064; Schlegel et al. (1996) *J. Virol.* 70:6576–65887). In isolation, protein 3A interacts with endoplasmic reticulum (ER) membranes to inhibit protein transport from the ER to the Golgi apparatus (Doedens et al. (1995) *Embo J* 14:894–9; Doedens et al. (1997) *J. Virol.* 71:9054–9064).

Until the work described herein, the role of inhibition of ER-to-Golgi traffic during viral infection was as yet unknown One possibility was that inhibition of protein secretion results from construction of a structural scaffold for the viral-RNA replication complex. Poliovirus RNA replication occurs on the cytoplasmic surface of double-membraned vesicles that proliferate in virally infected cells (Bienz et al. (1987) *Virology* 160:220–226; Dales et al. (1965) *Virology* 26:379–389; Schlegel et al. (1996) *J. Virol.* 70:6576–6588). All of the viral proteins required for RNA replication (2B, 2BC, 3A, 3AB, 3CD, and 3D) are physically associated with these vesicles in infected cells (Bienz et al. (1992) *J. Virol.* 66:2740–2747; Bienz et al. (1994) *Arch. Virol. Suppl.* 9:147–157). Another possibility was that inhibition of protein secretion is not required for RNA replication complex function, but is a virulence factor that enhances viral infection in tissues and animals. Consistent with the second hypothesis, the functions of 3A in viral RNA replication and in inhibiting protein secretion can be genetically separated Specifically, a mutant poliovirus, 3A-2 (Bernstein et al. (1988) *J. Virol.* 62:2922–2928), contains a mutation in the 3A protein that renders it much less efficient at blocking ER-to-Golgi traffic (Doedens et al (1997) *J. Virol.* 71:9054–906441), yet only causes a slight growth defect. However, this previous line of investigation did not definitively identify the role of 3A proteins, leaving both possibilities open. For example, other groups reported that recombinat, intact poliovirus genomes constructed to express an exogenous antigen induced protective CTL mediated immunity (Mandi et al. (1998) *Proc. Natl. Acad. Sci. USA* 95:8216–8221). However, the amount of this CTL response was not quantified, and the experimental system was chosen so that even low levels of CTL response would be protective. Therefore, the role of picornaviral protein 3A in viral pathogenesis and in manipulation of the host cellular machinery is not understood.

To date, strategies using the poliovirus genome as a vectors for expression of other proteins or peptides have included live recombinant viruses that could replicate and spread within infected cells or organisms (Alexander et al. (1994) *Proc. Natl. Acad. Sci. USA* 91:1406–1410; Andino et al. (1994) *Science* 265:1448–1451; Burke et al. (1988) *Nature* 332:81–82; Mandl et al. (1998) *Proc. Natl. Acad. Sci. USA* 95:8216–8221; Mattion et al. (1994) *J. Virol.* 68:3925–3933) as well as RNA "replicons" that can only undergo one infectious cycle in target cells and tissues (Ansardi et al. (1994) 54:6359–6364; Poon et al. (1999) EMBO J. 18: 555–564). Advantages of poliovirus-based vectors include their decades of use in humans, their ease of administration, and their ability to induce protective antibody responses. The role of viral proteins in picornaviral infections would provide not only a better understanding of viral pathogenesis, but also insight as to how to develop recombinant viral vectors that provide for the desired immune response, conferring the ability to modulate (e.g., increase or decrese) inflammatory and CTL response. The present invention addresses these issues.

SUMMARY OF THE INVENTION

The invention features recombinant viral vectors that take advantage of the activity of picornaviral protein 3A in modulating cytokine secretion and antigen presentation on MHC Class I (MHC I), which in turn provides for modulation of a Th1-mediated immune response to the transfected host cell. Specifically, a recombinant viral vector comprising a sequence encoding picornaviral protein 3A provides for decreased cytokine production, decreased antigen presentation on MHC I and a decreased incidence of Th1-mediated immune response, while a recombinant picornaviral vector that comprises a mutant 3A protein provides for increased antigen presentation on MHC I and increased Th1-mediated immune response towards the transfected host cell. The invention also features methods of inducing humoral or cellular immunity using the vectors.

BRIEF DESCRIPTION OF THE DRAWINGS

FIG. 1 is a graph showing the effect of poliovirus protein 3A on target cell lysis by CTL that recognize an antigen in protein NS3/4. Chimpanzee B lymphoblastoid target cells were infected with wild type vaccinia (open circles), rVV-NS3/4 alone (filled squares) or co-infected with rVV-NS3/4 and rVV-GFP (filled circles) or rVV-NS3/4 and rVV-3A, GFP (filled triangles).

FIG. 2 is a FACS plot showing the amount of MHC-1 on target cell surfaces in the presence and absence of poliovirus 3A protein expression.

FIGS. 3A–3C are graphs showing the antigen- and MHC-I allele-specificity on the inhibition of antigen presentation by poliovirus 3A protein. Target cells were incubated with CTL T4 (panel A), T73 (panel B), or T84 (panel C) at an effector/target ratio of 20:1. Data are presented as the means of triplicate samples and the standard deviations are indicated.

FIG. 4 is a graph showing the effects of wild-type and 3A-2 mutant poliovirus infections on antigen presentation to CTL. Chimpanzee target cells were infected with wild-type vaccinia (wt VV), rVV-NS3/4, wild-type poliovirus (wt polio), 3A-2 mutant poliovirus (3A-2 polio), or co-infected with rVV-NS3/4 and rVV-GFP, rVV-NS3/4 and rVV-3A, GFP, rVV-NS3/4 and wild-type poliovirus bracketed columns), or rVV-NS3/4 and 3A-2 poliovirus. Data are presented as the means of triplicate samples and the standard deviations are indicated.

FIG. 5 is a FACS plot showing the effect of wild-type and 3A-2 mutant poliovirus infections on MHC-I cell surface turnover.

FIGS. 6A–6D are graphs showing the effects of protein 3A on interferon-beta secretion (FIG. 6B), IL-6 secretion (FIG. 6C), and IL-8 secretion (FIG. 6D). FIG. 6A is a graph showing the results of a control experiment to illustrate that wildtype virus (WT) and the 3A-2 mutant virus (3A-2) replicate at substantially similar rates.

FIG. 7 provides an alignment of amino acid sequences for protein 3A of human poliovirus type 1 (Polio_1) (SEQ ID NO:1), mutant poliovirus 3A-2 (Polio_3A2) (SEQ ID NO:2), coxsackievirus B3 (Cox_B3) (SEQ ID NO:3), human rhinoviruses types 14, 16, and 2 (HRV_14, HRV_16, and HRV_2) (SEQ ID NOs:4, 5, and 6, respectively), encephalomyocorditis virus (EMCV) (SEQ ID NO:7), two strains of Theiler's virus (Th BeAn, TH GDVII) (SEQ ID NOs:8 and 9, respectively) and two strains of hepatitis A virus (HAV HM175 and HAV FG) (SEQ ID NOs:10 and 11, respectively).

FIGS. 8A–8D are FACS plots showing the recovery of cell-surface expression of anti-phOx single-chain antibody following protease treatment in HeLa cells in the absences of fluorescent probe (FIG. 8A), after labeling with BSA conjugated to phOx and fluorescein (BSA-FL-phOx) (FIG. 8B); after treatment with 10 mg/i trypsin and labeling with BSA-FL-phOx (FIG. 8C); or after trypsin treatment incubation at 37 deg. C for 3 hrs, and labeling with BSA-FL-phOx.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of such cells and reference to "the polynucleotide" includes reference to one or more polynucleotides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

"Polynucleotide" as used herein refers to an oligonucleotide, nucleotide, and fragments or portions thereof and to DNA or RNA of genomic or synthetic origin which can be single- or double-stranded, and represent the sense or antisense strand. Where "polynucleotide" is used to refer to a specific polynucleotide sequence (e.g. a picornavirus 3A protein-encoding polynucleotide), "polynucleotide" is meant to encompass polynucleotides that encode a polypeptide that is functionally equivalent to the recited polypeptide, e.g., polynucleotides that are degenerate variants, or polynucleotides that encode biologically active variants or fragments of the recited polypeptide, including polynucleotides having substantial sequence similarity or sequence identity relative to the sequences provided herein.

Similarly, "polypeptide" or "protein" (e.g. as in 3A protein) is meant to encompass an amino acid sequence of a naturally-occurring protein molecule, as well as variants thereof retaining an activity of interest (e.g., inhibition of antigen presentation on MHC I molecules, reduction in secretion of a cytokine (e.g., interferon-beta, IL-6, 8) and the like). Thus "polypeptide," "protein," and like terms are not meant to limit the amino acid sequence to the complete, native amino acid sequence associated with the recited protein molecule, but instead is meant to also encompass biologically active variants or fragments, including polypeptides having substantial sequence similarity or sequence identity relative to the amino acid sequences provided herein, including those polypeptides of different viral families, genuses, species, etc.

As used herein, "3A protein" or "protein 3A" refers to an amino acid sequence of a recombinant or nonrecombinant polypeptide having an amino acid sequence of i) a native 3A protein, ii) a biologically active fragment of a 3A protein, iii) biologically active polypeptide analogs of a 3A protein, or iv) a biologically active variant of an 3A protein. 3A proteins useful in the present invention, as well as nucleic acid encoding such 3A proteins, can be obtained from any suitable source, generally from a virus of the Picornaviridae family, or can be generated using standard recombinant techniques.

"Heterologous" as used herein is meant to indicate that the material is from an origin different than that of the surrounding material. For example, a viral vector comprising a "heterologous protein 3A encoding sequence" thus comprises a sequence encoding protein 3A that is of an origin different from at least one other portion of the viral vector.

"Recombinant" as used in the context of recombinant nucleic acid molecules (e.g., recombinant DNA or recombinant RNA) means that the nucleic acid sequence referred to is linked to another nucleic acid sequence(s) with which it is not normally linked in nature.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

The term "treatment" is used herein to encompass any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

By "individual," "host," "subject" or "patient" is meant any subject, generally mammalian, for whom delivery of a vector described herein is desired Human subjects are of particular interest; other subjects may include cattle, dogs, cats, guinea pigs, rabbits, rats, mice, horses, and so on.

Overview

The present invention is based on the discovery that picornavirus protein 3A inhibits presentation of antigens on MHC class I (MHC I) and inhibits the secretion of cytokines that promote inflammation (e.g., interferon-beta, IL-8, IL-6 and the like). Inhibition of MHC I antigen presentation results in a decrease in the cellular-mediated inflammatory response (e.g., a reduction in Th1-mediated inflammation).

Thus in one embodiment, the invention encompasses use of picornavirus 3A protein-encoding sequences in viral vectors, where use of the viral vectors provides for a decreased Th1-mediated inflammatory response relative to viral vectors without protein 3A. Such vectors are useful in, for example, vaccination to induce a primarily humoral (Th2-mediated) response, and for delivery of an endogenous or exogenous gene product to a host cell where Th1-mediated immunity against the host cell is undesirable.

In another aspect, the invention encompasses use of picornaviral vectors that include both a nucleotide sequence encoding an exogenous polypeptide and a nucleotide sequence encoding a mutant 3A protein, such that presentation of the exogenous polypeptide is not inhibited. Such vectors are useful for eliciting a cellular immune response in a host to antigens such as antigens of an intracellular pathogen, and self antigens, such as those associated with a tumor.

Specific aspects of the invention will now be described in more detail.

Picorna Viral 3A Proteins, 3A Protein Variants, and 3A Protein Mutants

The nucleic acid sequences encoding 3A protein can be obtained from any suitable picornaviral genome using recombinant techniques or can be produced by synthetic techniques. Any picornavirus can serve as the source of the sequence for the 3A protein-encoding sequence. Such picornaviruses include polioviruses, coxsackie viruses, rhinoviruses, and echoviruses. Exemplary nucleotide and amino acid sequences of 3A proteins suitable for use in the invention are publicly available, and methods for their recombinant manipulation well known in the art. Examples of protein 3A-encoding sequences include, but are not limited to, human poliovirus type 2 (Lansing strain), complete genome (GenBank Accession No. M12197, protein 3A encoded by residues 5110–5370); human poliovirus 2 (GenBank Accession No. D00625, protein 3A encoded by residues 5110–5370); human poliovirus 1 (GenBank Accession No. V01150; protein 3A encoded by residues 3386–5110); human poliovirus type 3 (GenBank Accession No. X04468, protein 3A encoded by residues 5106–5366); human poliovirus type 3 (GenBank Accession No. X00925); human poliovirus type 3 (GenBank Accession No. X00596); human poliovims type 3 (GenBank Accession No. X01076); coxsackievirus A21 (GenBank Accession No. D00538; protein 3A encoded by residues 5071–5331); and coxsackievirus A24 (GenBank Accession No. D90457). For additional picornaviral genomic sequences, which include sequences encoding protein 3A, see, e.g., PCT Publication No. WO 98/11133. Amino acid sequences of further exemplary picornaviral 3A proteins are provided in FIG. 7.

Variants and mutants of 3A protein are also of interest. In some embodiments, variants that retain ability to inhibit ER-to-Golgi trafficking are of interest. In other embodiments, mutants that exhibit a reduced capacity to inhibit ER-to-Golgi trafficking, relative to a wild-type 3A protein, but which do not substantially reduce viral replication, are of interest. Variant and mutant 3A proteins include those having one or more amino acid substitutions, insertions, or deletions relative to a wild-type 3A protein.

Variant and mutant 3A proteins can be generated by random mutagenesis or targeted mutagenesis of nucleic acid molecules encoding a 3A protein, using well-known techniques which are routine in the art. Techniques for in vitro mutagenesis of cloned nucleic acid molecules are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual,* CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Variant and mutant 3A proteins can also be selected from naturally-occurring mutations, mutations generated by radiation, mutations generated by random mutagenesis, and the like.

The ability of a picornavirus 3A protein, or any variant thereof, to inhibit MHC I antigen presentation can be examined using the assay described below. In addition, in some embodiments it is desirable to provide a picornaviral vector that does not substantially affect the secretory pathway, and thus does not affect MHC I antigen presentation Such 3A protein variants or mutated picornaviral vectors can be identified using the assay described below, and selected for protein secretion in the host cell.

Assay for Identification of Picornaviral Protein 3A Variants that Substantially Retain the Ability to Inhibit Antigen Presentation on MHC-I As discussed above, picornaviral 3A proteins that inhibit MHC I antigen presentation and are suitable for use in viral vectors for eliciting a predominantly humoral immune response, as well as variants of such 3A proteins that retain the ability to inhibit antigen presentation can be obtained by screening picornaviruses containing such candidate 3A proteins using a selection scheme based on disruption of the secretory pathway in a host cell infected with a test virus. This assay can also be used to identify picornaviral vectors that do not substantially affect MHC I antigen presentation, and thus are suitable for eliciting a cellular immune response.

The ability of protein 3A to affect the secretory pathway can be assayed using a host cell line constructed to constitutively express a cell surface molecule that can be easily detected by, for example, its binding to a detectable label. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. The detectable label may be attached, directly, or indirectly, to a substrate or ligand for the protein being detected. Where the protein being detected is a first member of a specific binding pair (e.g., receptor/ligand, antibody/antigen, and the like), the second member of the specific binding pair can be labeled directly or indirectly. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (Antibodies: *A Laboratory Manual* (1988) Cold Spring Harbor Laboratory Press, Cold Spring Harbor, N.Y.)).

As one non-limiting example, the cell surface molecule can be a single-chain antibody that recognizes a specific antigen (e.g., a hapten) so that antibody-antigen complexes can be readily detected on the cell surface. For FACS analysis, cells can be stained with BSA conjugated to both phOx and fluorescein.

Candidate 3A proteins are screened in a vector that provides for expression of the candidate protein in the cell cytoplasm The vector is introduced into the host cell, the cell treated to remove cell surface molecules, and the return of the cell surface molecule to the surface of the host cell detected after a suitable time has passed. If expression of the candidate 3A protein in the host cell results in little or no detectable cell surface molecule after a period of time suitable for return of the cell surface molecule to the cell surface in a control cell, then the candidate 3A protein has activity in inhibition of the secretory pathway (Sec−) and is suitable for use in vectors in connection with eliciting a primarily humoral immune response. If expression of the candidate 3A protein in the host cell results in the presence of cell surface molecule on the cell surface, then the candidate 3A protein is defective for inhibition of the secretory pathway (Sec+) and is suitable for use in lieu of naturally-occurring protein 3A in picornaviral vectors useful in connection with eliciting cellular immune response.

Assay for Identification of Picornaviral 3A Protein Mutants that Exhibit a Reduced Ability to Inhibit ER-to-Golgi Trafficking The selection scheme described above is also useful in obtaining mutant picornaviruses that support the viral replicative cycle but exhibit a reduced ability, relative to a wild-type picornaviral 3A protein, to inhibit ER-to-Golgi traffic, e.g., to obtain Sec+ picornaviruses with wild-type growth characteristics. Mutant 3A proteins that exhibit a reduced ability to inhibit ER-to-Golgi trafficking exhibit a reduction in inhibition of antigen presentation by MHC I, relative to a wild-type picornaviral 3A protein, e.g., a mutant 3A protein exhibits less than about 75%, less than about 50%, less than about 40%, less than about 30%, less than about 25%, or less than about 10% of the inhibition of antigen presentation by MHC I than a wild-type picornaviral 3A protein. Thus, the assay can be used to identify the genetic lesions that result in 3A proteins that do not substantially affect the secretory pathway and/or do not substantially affect MHC I antigen presentation. Once the genetic lesions are known, stable mutant picornaviruses can be generated by, for example, making double-nucleotide rather than single-nucleotide substitutions to yield the same amino acid change(s), or by generating deletion variants. Genetic stability of the mutant viruses can be assessed by passage in tissue culture and in susceptible mice transgenic for the poliovirus receptor (Ren et al. (1990) *Cell* 63:353–361).

Recombinant Viral Vectors

The invention encompasses at least two types of vectors that take advantage of the discovery that picornaviral protein 3A inhibits antigen presentation on MHC I and the secretion of pro-inflammatory cytokines: 1) vectors comprising a recombinant protein 3A sequence for use in delivery of gene products to a host cell where a Th1-mediated inflammatory response is not desirable (e.g. in vectors designed to promote humoral immunity or delivery of a gene product for gene therapy); and 2) vectors based on picornaviral genomes express mutant 3A protein that exhibit a reduced ability to inhibit protein secretion, which vectors are useful in delivery of gene products to provide for induction of cell-mediated immunity (e.g., as in vaccines for HW).

In general, vectors comprising a sequence encoding a functional recombinant protein 3A sequence can be used to avoid or reduce inflammation mediated by Th1, to avoid or reduce interferon-beta (IFN-β) production, reduce or avoid IL-6 production, and/or reduce or avoid IL-8 production otherwise associated with delivery of a vector that does not comprise a function protein 3A-encoding sequence competent to inhibit protein secretion. Each of IFN-β, IL-6 and IL-8 have antiviral effects in infected hosts, and the functional production of each in response to viral infection requires new transcription and translation, as well as secretion from the infected cell. Once synthesized and secreted into the extracellular milieu, interferon-β (and interferon-α) binds to membrane receptors, triggering a series of signal transduction events which lead to the transcriptional induction of many genes, including the interferon genes themselves. Therefore, the secretion of interferons can induce an antiviral state not only in infected cells but in nearby cells as well (for a review, see Vilcek et al. 1996. Interferons and other cytokines. In B. N. Fields, D. M. Knipe and P. M. Howley (ed), Fields Virology. Lippincott-Raven Publishers, Philadelphia, Pa. 375–399). IL-6 is known to promote differentiation of B cells and therefore promote antibody production (for a review, see Lucey et al. (1996) *Clin. Microbiol. Rev.* 9:532–562), and IL-8 attracts neutrophils to the site of infection and promotes their adherence to infected tissues (for a review, see Harada et al. (1996) *Molec. Med. Today* 2:482–489). These three secreted cytokines are merely representative; there are likely to be many more induced and secreted proteins with potential antiviral effects whose production is inhibited by the wild-type function of 3A.

Such vectors comprising a sequence encoding functional recombinant protein 3A can also be used where it is desirable to elicit and/or enhance Th2-mediated immune response to an antigen encoded by the vector. Furthermore, vectors comprising a sequence encoding a functional protein 3A may be useful in applications other than vaccines, e.g., in delivery of gene products in the context of gene therapy, particularly where Th1-mediated inflammation has proven problematic and where gene product secretion is not essential to the delivery of the encoded gene product of interest.

Recombinant picornaviral vectors that contain specific mutations in protein 3A find particular use where a cellular response to an antigen encoded by the vector is desirable. For example, a cellular immune response may be desirable where the recombinant picornaviral vector encodes an antigen normally found on the surface of cells infected by the pathogen and where clearance of the pathogen can be accomplished by antigen-specific cell-mediated immunity. A cellular immune response is also desirable where the recombinant picornaviral vector encodes a tumor-associated antigen, where reduction in the number of tumor cells can be accomplished by cell-mediated immunity specific for the tumor-associated antigen.

Whether a vaccine should stimulate a strong cellular immune response or not depends on the pathogenesis of the microorganism in question For example, for HIV infections, it is thought that a strong cellular immune response could be critical in eliminating virally infected cells. Furthermore, because CTL epitopes are less variable than those recognized by antibodies, an HIV vaccine that elicited a strong CTL response might prove effective against a wider spectrum of HIV strains and variants (reviewed in Heilman (1998) *Nature Med.* 4:532–534). On the other hand, the tissue damage caused by, for example, some *Mycobacterium leprae* infections is mediated by $CD8^+$ cytotoxic T cells (reviewed in de Vries (1991) *Amer. J. Trop. Med. Hyg.* 44:12–16). Therefore, a good vaccine candidate in this latter case would be one that elicits an effective antibody response, without eliciting the strong CTL responses that might exacerbate inflammation. The present invention takes advantage of the discovery that protein 3A modulates antigen presentation on MHC I to design picornaviral vectors that provide for stimulation of the cellular immune response to varying extents by modulating the function of 3A, thereby tailoring the recombinant vaccines.

Recombinant Vectors Comprising a Functional Picornaviral 3A Protein-Encoding Sequence for Induction of a Predominantly Humoral Immune Response In general, a sequence encoding a picornaviral 3A protein can be incorporated into any of a variety of vectors suitable for use in expression of an encoded gene product of interest in a host cell, particularly where the vector provides for expression of the encoded gene product in the host cell cytoplasm and where presentation of antigens on the host cell surface MHC I and/or stimulation of Th1-mediated inflammation is undesirable.

The nucleic acid vector into which the 3A protein-encoding sequence is incorporated may be of viral or non-viral origin (see e.g., Jolly, *Cancer Gene Therapy* (1994) 1:51; Kimura, *Human Gene Therapy* (1994) 5:845; Connely, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

In general, the vectors of the invention comprise 1) an exogenous nucleic acid sequence for expression in the host cell (e.g., encoding an antigenic polypeptide); 2) a promoter operably linked to the exogenous nucleic acid sequence; and 3) a recombinant picornaviral protein 3A-encoding sequence, which sequence is generally operably linked to a promoter for expression of protein 3A.

The exogenous sequence for expression in the host cell can be any of a variety of nucleic acid sequences of interest Where the vector is to be used as a vaccine, the exogenous sequence encodes an antigenic polypeptide that comprises an epitope against which a humoral immune response is desired. Such antigenic polypeptides include, but are not necessarily limited to polypeptides comprising immunogenic sequences of pathogenic viruses (e.g., respiratory syncytial virus (RSV), hepatitis C virus (HCV) hepatitis A virus, hepatitis B virus, herpes simplex virus (e.g., HSV type 1), influenza virus, human immunodeficiency virus (e.g., gp120), rotavirus (e.g., VP3, VP7), rotavirus; rabies virus, and the like), bacteria (e.g., *Mycobacterium leprae, Vibro cholera, Streptococcus, Staphylococcus,* and the like), parasites (e.g., *Plasmodium falciparum, Trypanosoma cruzi, Trypanosoma falciparum*), and other pathogenic organisms against which a humoral immune response and a limited CTL response may provide protection, therapeutic advantage, and/or facilitate clearance (e.g., through killing) of an infecting pathogen.

The term "epitope" is not meant to be limited to only the sequence of amino acids to which is attributed the capacity for inducing in vivo antibodies against the antigen from which this epitope has been taken, but should be understood to encompass, where appropriate, shorter or longer amino acid sequences which, normally, surround the epitope (in the restricted sense of the term) in the antigen from which it has been taken.

Exemplary viral vectors that can be modified to express picornaviral protein 3A according to the invention include, but are not necessarily limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), adeno-associated virus (AAV) vectors (see, e.g., WO 94/12649, WO 93/03769; WO 93/19191; WO 94/28938; WO 95/11984 and WO 95/00655), and poxvirus-based vectors (e.g., fowlpox, vaccinia, etc.). Delivery of these vectors to the host is accomplished by methods appropriate to the viral vector selected, and according to methods well known in the art (e.g., administration by injection (e.g., intramuscular, subcutaneous, intavenous, and the like), oral administration, etc.).

The discovery upon which the invention is based can also be applied to non-viral vectors, e.g., in the context of DNA-based vaccination, gene therapy, and the like. In this context, the vector is delivered to the host using any of a variety of methods well known in the art. For example, using polycationic condensed DNA linked or unlinked to killed adenovirus alone (see, e.g., Curiel *Hum. Gene Ther.* (1992) 3:147); ligand-linked DNA (see, e.g., Wu, *J. Biol. Chem.* (1989) 264:16985); liposomes (U.S. Pat. No. 5,422,120; WO 95/13796; WO 94/23697; WO 91/14445; and EP 0524968); and the like. The vector can be encapsulated in a viral particle; complexed with a polymer; or formulated with a cationic compound. The vector can also be administered as naked DNA, e.g., according methods are described in WO 90/11092 and U.S. Pat. No. 5,580,859.

Recombinant Picornaviral Vectors Deficient in Biologically Active Picornaviral 3A Protein Production for Induction of a Cellular-Mediated Immune Response In a second embodiment, the recombinant viral vector of the invention is based upon a picornaviral genome and provides for reduced antigen presentation on MHC I relative to conventional picornaviral vectors. In this embodiment, the recombinant vector is based upon a picornaviral genome that encodes mutant 3A protein that exhibits a reduced ability, relative to a wild-type picornaviral 3A protein, to inhibit host protein secretion Rendering a picornaviral sequence mutant in protein 3A can be accomplished by any of a variety of methods well known in the art. The sequence can be mutated to render the encoded gene product nonfunctional in the inhibition of protein secretion, but competent for the other aspects of 3A function in viral infection.

The picornaviral vector can be based upon any picornaviral genome, e.g., poliovirus, rhinovirus, echovirus, or coxsackie virus. Examples of picornaviral vectors that express mutant 3A proteins according to the invention include, but are not necessarily limited to those described in U.S. Pat. No. 5,965,124 (polioviral vectors); U.S. Pat. No. 5,182,211; (picornaviral vectors); U.S. Pat. No. 5,714,374 (rhinoviral vectors) U.S. Pat. No. 5,541,100 (rhinoviral vectors); PCT Publication Nos. WO 94/26900 (picornaviral vectors); WO 89/01516 (picornaviral vectors); WO 2000/08166 (poliovirus vaccine).

In general, the vectors in this embodiment of the invention comprise at least a portion of a picornaviral genome and a sequence encoding an exogenous antigen positioned within the genome for expression in the host cell, wherein the picornaviral sequence encoding protein 3A is mutated to render the encoded protein 3A nonfunctional in the inhibition of protein secretion.

In general, the exogenous antigens in this embodiment are antigens to which it is desirable to elicit a Th1-mediated immune response, e.g., to provide for stimulation of an antigen-specific Th1-mediated immune response. Examples of the source of such exogenous antigens include, but are not necessarily limited to, viruses (e.g., respiratory syncytial virus, rotavirus, human immunodeficiency virus, and the like); bacteria (e.g., *Listeria, Mycobacteria* (e.g., *M. tuberculosis*), *Shigella,* and the like); parasites (e.g., *Plasmodium falciparum, Giardia, Trypanosama cruzi* and the like); tumors (e.g., tumor-associated antigens (TAA), cell surface proteins differentially expressed on cancerous cells relative to normal, non-cancerous cells, and the like).

In many embodiments, the exogenous polypeptide is an antigenic polypeptide of a microbial pathogen. Such recombinant vectors can then be administered to a host to prevent or treat infection by the pathogen, or to prevent or treat symptoms of such pathogenic infection. Of particular interest in some embodiments is the prevention or treatment of infection or disease caused by microbial pathogens that, during the course of infection, are present intracellularly, e.g., viruses (e.g., HIV), bacteria (e.g., *Shigella, Listeria, mycobacteria,* and the like), parasites (e.g., malarial parasites (e.g., *Plasmodium falciparum*), trypanosomes, and the like), etc.

Antigenic polypeptides of such microbial pathogens are well known in the art, and can be readily selected for use in the present recombinant vector by the ordinarily skilled artisan. Polypeptides and peptide epitopes associated with intracellular pathogens are known in the art and include, but are not limited to, antigens associated with human immunodeficiency virus, e.g., HIV gp120, or an antigenic fragment thereof; cytomegalovirus antigens; *Mycobacterium* antigens (e.g., *Mycobactenium avium, Mycobacterium tuberculosis,* and the like); *Pneumocystic carinii* (PCP) antigens; malarial antigens, including, but not limited to, antigens associated with *Plasmodium falciparum* or any other malarial species, such as 41-3, AMA-1, CSP, PFEMP-1, GBP-130, MSP-1, PFS-16, SERP, etc.; fungal antigens; yeast antigens (e.g., an antigen of a Candida spp.); toxoplasma antigens, including, but not limited to, antigens associated with *Toxoplasma gondii, Toxoplasma encephalitis,* or any other *Toxoplasma* species; Epstein-Barr virus (EBV) antigens; and the like.

Whether an immune response has been elicited to a pathogenic organism can be determined (quantitatively, e.g., by measuring a parameter, or qualitatively, e.g., by assessing the severity of a symptom, or by detecting the presence of a particular parameter) using known methods. Methods of measuring an immune response are well known in the art and include enzyme-linked immunosorbent assay (ELISA) for detecting and/or measuring antibody specific to a given pathogenic organism; and in vitro assays to measure a cellular immune response (e.g., a CTL assay using labeled, inactivated cells expressing the epitope on their cell surface with MHC Class I molecules). Whether an immune response is effective to facilitate protection of the host against infection, or symptoms associated with infection, by a pathogenic organism can be readily determined by those skilled in the art using standard assays, e.g., determining the number of pathogenic organisms in a host (e.g., measuring viral load, and the like); measuring a symptom caused by the presence of the pathogenic organism in the host (e.g., body temperature, $CD4^+$ T cell counts, and the like).

In other embodiments, a polypeptide antigen expressed on a given tumor cell (e.g., a tumor associated antigen; "TAA") is inserted into a recombinant vector of the invention. Such recombinant vectors can be administered to an individual having, or suspected of having, a tumor. In some cases, such recombinant vector can be administered to an individual who does not have a tumor, but in whom protective immunity is desired. As is often the case, the immune system does not mount an immune response effective to inhibit or suppress tumor growth, or eliminate a tumor altogether. Tumor-associated antigens are often poorly immunogenic; perhaps due to an active and ongoing immunosuppression against them. Furthermore, cancer patients tend to be immunosuppressed, and only respond to certain T-dependent antigens. In these cases, introduction into the host of a recombinant vector of the invention which expresses an exogenous peptide corresponding to an antigen expressed on the tumor cell surface can elicit an immune response to the tumor in the host. Whether tumor cell growth is inhibited can be determined using any known assay, including, but not limited to, counting the number of tumor cells, measuring tumor mass, measuring the level of a TAA in a bodily fluid, and the like.

The entire TAA may be, but need not be, included in the vector. Instead, a portion of a TAA, e.g., an epitope, particularly an epitope that is recognized by a CTL, may be inserted. Tumor-associated antigens (or epitope-containing fragments thereof) which may be inserted into a subject recombinant vector include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV18, TUAN, alpha-feto protein (AFP), OFP, CA-125, CA-50, CA-19-9, renal tumor-associated antigen G250, EGP40 (also known as EpCAM), S100 (malignant melanoma-associated antigen), p53, prostate tumor-associated antigens (e.g., PSA and PSMA), and p21ras.

Formulations, Routes of Administration, and Dosages
  Formulations

The invention further provides pharmaceutical formulations comprising a recombinant vector of the invention.

Pharmaceutical compositions can be prepared in various forms, such as granules, tablets, pills, suppositories, capsules, injectable formulations, suspensions, sprays, suppositories, transdermal applications (e.g., patches, etc.), salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Pharmaceutical grade organic or inorganic carriers and/or diluents suitable for oral and topical use can be used to make up compositions containing the recombinant vector. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

For oral preparations, the formulations can be used alone or in combination with appropriate additives to make tablets, powders, granules or capsules, for example, with conventional additives, such as lactose, mannitol, com starch or potato starch; with binders, such as crystalline cellulose, cellulose derivatives, acacia, corn starch or gelatins; with disintegrators, such as com starch, potato starch or sodium carboxymethylcellulose; with lubricants, such as talc or magnesium stearate; and if desired, with diluents, buffering agents, moistening agents, preservatives and flavoring agents.

The vectors can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The recombinant viral vectors of the invention may also be formulated with various stabilizers. Any suitable stabilizer can be used including carbohydrates such as sorbitol, mannitol, starch, sucrose, dextrin, or glucose; proteins such as albumin or casein; and buffers such as alkaline metal phosphate, and the like. A stabilizer is particularly advantageous when a dry vaccine preparation is prepared by lyophilization.

The vectors can be utilized in aerosol formulation to be administered via inhalation The vectors of the present invention can be formulated into pressurized acceptable propellants such as dichlorodifluoromethane, propane, nitrogen and the like. Furthermore, the vectors can be made into suppositories by mixing with a variety of bases such as emulsifying bases or water-soluble bases. The vectors of the present invention can be administered rectally via a suppository. The suppository can include vehicles such as cocoa butter, carbowaxes and polyethylene glycols, which melt at body temperature, yet are solidified at room temperature.

When used as an immunogenic composition (e.g., a "vaccine"), a recombinant vector of the invention can be formulated in a variety of ways. In general, the immunogenic composition of the invention is formulated according to methods well known in the art of vaccine preparation, using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a vaccine composition of the invention may be formulated to contain other components, including, e.g., adjuvants, stabilizers, pH adjusters, preservatives and the like. Such components are well known to those of skill in the vaccine art. Adjuvants include, but are not limited to, aluminum salt adjuvants (Nicklas (1992) *Res. Immunol.* 143:489–493); saponin adjuvants; Ribi's adjuvants (Ribi ImmunoChem Research Inc., Hamilton, Mont.); Montanide ISA adjuvants (Seppic, Paris, France); Hunter's TiterMax adjuvants (CytRx Corp., Norcross, Ga.); Gerbu adjuvants (Gerbu Biotechnik GmbH, Gaiberg, Germany); and nitrocellulose (Nilsson and Larsson (1992) Res. Immunol. 143: 553–557). In addition, other components that may modulate an immune response may be included in the formulation, including, but not limited to, cytokines, such as interleukins; colony-stimulating factors (e.g., GM-CSF, CSF, and the like); and tumor necrosis factor.

Routes of Administration

Conventional and pharmaceutically acceptable routes of administration include intranasal, intramuscular, intratracheal, intratumoral, subcutaneous, intradermal, vaginal, intrapulmonary, intravenous, rectal, nasal, oral and other parenteral routes of administration. Routes of administration may be combined, if desired, or adjusted depending upon the antigenic peptide or the disease. The composition can be administered in a single dose or in multiple doses, and may encompass administration of booster doses, to elicit and/or maintain immunity.

When they are used as vaccines, the recombinant vectors of the present invention are administered to an individual using known methods. They may, e.g., be administered by the same routes by which conventional (presently-available) vaccines are administered and/or by routes that mimic the route by which infection by the pathogen of interest occurs.

It should be noted that the term "vaccines" (used interchangeably herein with "immunogenic composition") is not meant to be limiting. Vaccines are generally considered to be pharmaceutical formulations of viruses or viral vectors that when administered to a subject, can stimulate the body to produce a humoral or cell-mediated immune response specific for an antigen of a pathogenic organism However, although the induced immune response can in some cases prevent the onset of the clinically recognized disease state, this need not necessarily be the case. Vaccines may, when administered to a patient before infection by a pathogenic virus, only slow down or otherwise inhibit, but not prevent, the patient from exhibiting clinical symptoms of infection. Furthermore, vaccines may be administered to a patient after infection by a pathogenic virus or the development of a cancerous tumor, and to some extent stimulate the body's immune response against the infection or tumor. Thus, in the context of vaccination against cancer or against an intracellular pathogen (e.g. HIV), the vaccine does not necessarily prevent cancer or a pathological condition caused by or associated with the intracellular pathogen (e.g. AIDS) in a vaccinated subject, but rather can provide treatment to slow or otherwise inhibit metastasis or further metastasis or the onset of AIDS, at least to some extent.

Dosages

The vaccine according to the present invention is administered in amounts sufficient to stimulate the immune system against the antigenic exogenous polypeptide of the vector. The vaccine is generally administered in dosages ranging from about $10^2$ to about $10^{10}$ viral particles, more generally from about $10^3$ to about $10^6$ viral particles, depending on the amount of replication expected in the host.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following procedures are used in several of the Examples described in detail below.

Chimpanzee cell lines and vaccinia expression vectors. The chimpanzee B lmphoblastoid cell lines, CTL cell lines and recombinant vaccinia that express HCV proteins used in this study have been previously described (Cooper et al. (1999) *Immunity* 10:439–449). B lymphoblastoid cell lines were grown in RPMI-1640 with 10% fetal bovine serum (Gibco-BRL, Grand Island, N.Y.). CTL were grown in a T-cell medium composed of RPMI-1640, 100U/ml recombinant IL-2 (a generous gift from Chiron Corp., Emoryville, Calif.), 5% human T-Stim (Collaborative Biomedical Products, Bedford, Mass.), and 10% fetal bovine serum CTL were re-stimulated for growth every 10–14 days with irradiated human peripheral blood mononuclear cells as previously described (Erickson et al. (1993) *J. Immunol* 151: 4189–4199).

To make recombinant vaccinia viruses that express poliovirus 3A and GFP from a dicistronic mRNA (rVV-3A,GFP), the wild type poliovirus 3A coding sequence, the poliovirus IRES, and the coding sequence for an enhanced GFP (Cormack et al. (1996) *Gene* 173:33–38) were amplified by PCR, ligated together, and inserted into a plasmid termed pTRE-3A,GFP. The 3A-IRES-GFP fragment was excised from the cloning vector with EcoRI and XbaI and inserted into EcoRI-NheI digested pRB21, a shuttle vector for vaccinia recombination (Blasco et al. (1995) *Gene* 158:157–162). BSC-1 cells were transfected with pRB21-3A,GFP and infected with the plaque-deficient vaccinia virus, vv-RB12 (Blasco et al. (1995) *Gene* 158:157–162). Individual plaques of recombinant vaccinia were isolated and expression of poliovirus 3A protein and GFP were confirmed by immunoblot A recombinant vaccinia that expresses GFP in the absence of 3A protein was constructed using a similar strategy except that the 3A coding sequences were omitted.

$^{51}$Cr-release assays. Standard chromium-release assays for cytolytic activity were performed as follows (modified from Wunderlich et al. (1997) *Induction and measurement of cytotoxic T lymphocyte activity* (John Wiley & Sons, New York): target cells were infected with vaccinia expression vectors at a multiplicity of infection of 10. At 12 h post-infection, $5\times10^5$ infected cells were harvested, washed in medium, resuspended in 200 μl medium, and labeled with 50 μCi $Na_2{}^{51}CrO_4$ (Amersham, Piscataway, N.J.) for 1 h Labeled cells were washed three times in medium and resuspended to 50,000 cells/ml in T-cell medium. For each assay, 5000 target cells were incubated with the indicated number of CTL in round-bottomed 96-well plates in a final volume of 200 μl. At 4 h, 50 μl supernatant were removed and transferred to 96-well LumaPlates (Packard Instrument Co., Meriden, Conn.) and allowed to dry overnight. Radioactivity was assayed by reading LumaPlates in a scintillation microplate reader (PerkinElmer, Wellesley, Mass.). Spontaneous $^{51}$Cr release was determined by incubating labeled cells in the absence of CTL. Total label was measured by substituting 5% Triton X-100 for the CTL in T-cell medium.

Granzyme A secretion assays. Granzyme A secretion assays were modified from Kane et al. (Kane et al. (1989) *Nature* 340:157–159). Target cells were infected as for the $^{51}$Cr-release assays. At 12 h post-infection, infected cells were harvested and washed in medium For each assay, $1\times10^5$ target cells were combined with $1\times10^5$ CTL in a total volume of 250 μl in round-bottomed 96-well plates. After a 4 h incubation, 5 μl supernatant were added to 245 μl enzyme reaction mixture (0.2 mM N-benzyloxycarbonyl thiobenzylester, 0.22 mM 5,5'-dithiobis(2-nitrobenzoixc acid)) (Sigma Chemical Co., St. Louis, Mo.) in flat-bottomed 96-well plates. Light absorbance at 405 nm was measured at 30 min intervals in a microplate reader (Bio-Tek Instruments, Winooski, Vt.). The amount of enzyme was determined from the rate measured during the linear phase of the reaction. One unit of granzyme A was defined as the amount of enzyme required to convert the reaction mixture to $OD_{405}$=1 in 60 min.

Virus infection and FACS analysis. Chimpanzee B lymphoblastoid cells were infected with rVV-GFP or rVV-3A, GFP at a multiplicity of infection less than one. Wild type Mahoney type 1 poliovirus and 3A-2 mutant poliovirus (Bernstein et al. (1988) *J. Virol.* 62:2922–2928) infections were carried out at multiplicities of infection of 20 plaque-forming units/cell. At 12 h post-infection, $10^6$ cells were washed with PBS and resuspended in 200 µl PBS. Cells were labeled with W6/32 anti-human HLA mouse monoclonal antibody (Sigma Chemical Co., St Louis, Mo.) and visualized with a phycoerthryin-conjugated anti-mouse secondary antibody (Sigma Chemical Co., St Louis, Mo.). Cells were analyzed by FACS using a FACScan flow cytometer (BD Biosciences, San Jose, Calif.).

Example 1

Poliovirus 3A Protects Cells From CTL-Mediated Lysis

Cell lines generated during a study of hepatitis C virus (HCV) infection in chimpanzees (Cooper et al. (1999) *Immunity* 10:439–449) were used to study the effects of poliovirus 3A protein expression and poliovirus infection oil MHC-I dependent antigen presentation. This provides an example of the use of a wild-type picornaviral 3A protein in a nonhomologous vector (vaccinia virus) to reduce the amount of MHC-I dependent antigen presentation. This system was chosen because chimpanzees are natural hosts of poliovirus (Howe et al. (1941) *Bull Johns Hopkins Hosp* 69:149–181) and the cell biology and biochemistry of poliovirus has been studied most extensively in primate cells. CTL lines were derived from liver biopsies of an HCV-infected chimpanzee named Todd, who resolved the infection 11 weeks following inoculation (Cooper et al. (1999) *Immunity* 10:439–449). B lymphoblastoid cell lines were derived from the same individual for use as target cells to measure the cytolytic activity of the CTL lines. For these studies, four CTL lines that were characterized according to MHC-1 allotype and HCV epitope specificities were used (Cooper et al. (1999) *Immunity* 10:439–449).

To obtain expression of poliovirus 3A protein in all of the target cells, vaccinia expression vectors were constructed that expressed either green fluorescent protein (GFP) (Cormack et al. (1996) *Gene* 173:33–38) alone or both 3A and GFP from a dicistronic mRNA (rVV-GFP and rVV-3A,GFP, respectively). Expression of GFP and 3A in infected chimpanzee cells was detected as early as 1 h post-infection with rVV-3A-GFP as determined by immunoblot and remained at a relatively constant level throughout the course of infection (data not shown).

To express specific HCV antigens in the target cells, chimpanzee B lymphoblastoid cell lines were infected with recombinant vaccinia viruses that expressed various portions of the HCV polyprotein. The vaccinia expression vector, rVV-NS3/4, expresses an open reading frame that encodes amino acids 1590 to 2050 of HCV which spans the NS3/NS4 junction (rVV-NS3/4; Cooper et al. (1999) *Immunity* 10:439449). Co-infections of rVV-NS3/4 with rVV-GFP and with rVV-3A,GFP were performed to achieve HCV epitope expression in the presence or absence of co-expressed poliovirus protein 3A. At 12 h post-infection, the infected cells were labeled with $^{51}Cr$ and incubated with the CTL cell line T14, which specifically recognizes an HCV peptide from NS3 (amino acids 1629 to 1637 of the polyprotein) in the context of the Patr-B* 1701 MHC-I haplotype (Cooper et al. (1999) *Immunity* 10:439–449).

CTL-mediated lysis was observed in reactions containing target cells that were infected with either rVV-NS3/4 alone (filled squares) or co-infected with rVV-NS3/4 and rVV-GFP (filled circles) (FIG. 1). The observed lysis was antigen-dependent, as target cells infected with a wild-type vaccinia virus that encoded no HCV proteins were unaffected by incubation with the CTLs. However, cells co-infected with rVV-NS3/4 and rVV-3A,GFP were nearly completely protected from CTL-mediated lysis even at high CTL-to-target ratios (FIG. 1).

Example 2

Turnover of Cell-Surface MHC-I is Unaffected by Poliovirus Protein 3A

To test any effect of 3A protein expression on previously synthesized MHC class I molecules already at the plasma membrane, target cells were infected with either rVV-GFP or rVV-3A,GFP and the infections were allowed to proceed for 12 hours before harvesting and labeling with anti-MHC-I antibodies. The functional half-life of peptide-bound MHC-I on the cell surface is highly variable with an average of 5–10 h (Eberl et al. (1996) *Eur J Immunol* 26:1993–9). Vaccinia infections were performed at relatively low multiplicities of infection so that not all of the cells were infected, this allowed for direct comparison of infected and uninfected cells within each sample. At 12 h post-infection, the cells were stained with anti-MHC-I antibodies and analyzed by FACS. For each sample, $10^4$ cells were plotted for red (MHC-I) versus green (GFP) fluorescence.

GFP-expressing cells did not show any change in the amount of cell-surface MHC-I expression in either the absence or presence of poliovirus 3A protein expression (FIG. 2). Therefore, the protective effects of 3A from CTL-mediated lysis were due to inhibition of new antigen presentation rather than increased internalization of MHC-I from the cell surface.

Example 3

The Effects of 3A on Antigen Presentation are not Antigen or MHC-1 Specific

To test the effects of poliovirus 3A protein on other combinations of CTL and antigens, target cells were infected with recombinant vaccinia virus that expressed a portion of the HCV genome that encodes amino acids 364 to 1618 of the HCV polyprotein (rVV-E2/NS3; Cooper et al. (1999) *Immunity* 10:439–449). The cells were co-infected with rVV-E2/NS3 and either rVV-GFP or rVV-3A,GFP. At 12 h post-infection, cells were labeled with $^{51}Cr$ and incubated for 4 hrs with one of three CTL lines that recognize different HCV antigens in the context of the Patr-A*0601 haplotype at an effector/target ratio of 20:1. T4 (CTL T4 (panel A)) is specific for an epitope from HCV P7 (amino acids 781 to 791 of the polyprotein) and, although CTL cell lines T73 (panel B) and T84 (panel C) were independently isolated, they are both specific for the same epitope from HCV E2 (amino acids 651 to 665 of the polyprotein). Specific lysis was determined as above.

As with T14 CTL (FIG. 1), lysis by T4, T73, and T84 was antigen dependent (FIG. 3); target cells were efficiently lysed when infected with rVV-E2/NS3 alone or when co-infected with rVV-GFP. Co-infection with rVV-3A,GFP resulted in reduced lysis with all three CTL lines. These results showed that the protection from antigen-dependent CTL by 3A was not specific to any one antigen or MHC-I haplotype.

Example 4

Wild-Type 3A is Required for the Inhibition of Antigen-Dependent CTL Activation by Poliovirus To determine whether the effects of 3A protein on MHC-I presentation were relevant to poliovirus infection, chimpanzee target cells were infected with wild-type and mutant polioviruses. However, poliovirus-infected cells were poor targets in conventional $^{51}$Cr-release assays due to the increased permeability of their cell membranes (Doedens et al. (1995) *Embo J* 14:894–9; Lacal et al. (1983) *J Gen Virol* 64:787–93) and thus poor retention of the $^{51}$Cr label. Therefore, an assay for functional antigen presentation that is less dependent on the permeability of the target cell membrane was used. This assay, secretion of granzyme A from CTL, has been demonstrated to be an effective indicator of antigen-dependent CTL activation (Suhrbier et al. (1991) *J immunol Methods* 145:43–53).

To test the effects of poliovirus infection on antigen presentation and subsequent CTL activation, chimpanzee target cells were co-infected with rVV-NS3/4 and either rVV-GFP, rVV-3A,GFP, or Mahoney type1 wild-type poliovirus, and the infections were allowed to proceed for 12 h. At 12 h post-infection, target cells were incubated for 4 h with T14 CTL at an effector/target ratio of 1:1. Although poliovirus could successfully replicate in this cell line, host-protein synthesis remained active and very little lysis (<10%) was observed at 12 h post-infection.

Figure 4:
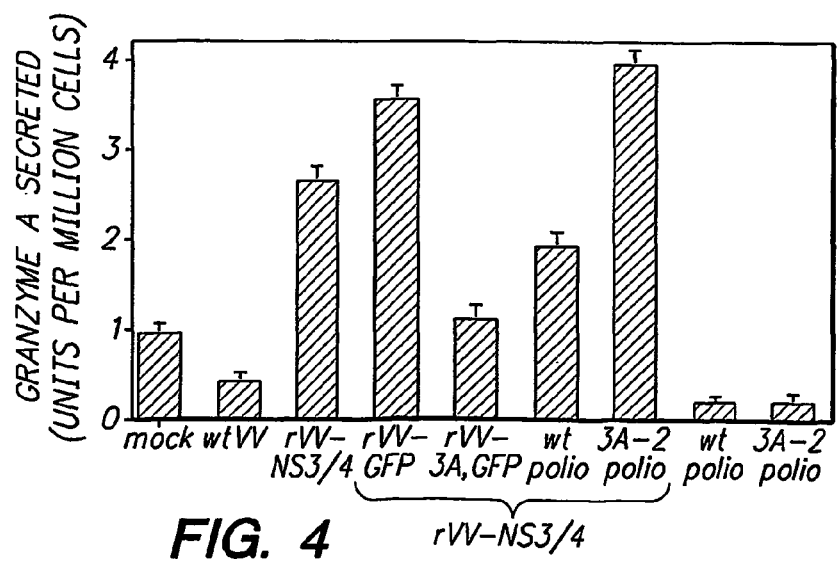

The abundance of 3A protein in the poliovirus-infected cells was about one-half that observed in the rVV-3A,GFP-infected cells (data not shown). The infected target cells were incubated with T14 CTL at an effector/target ratio of 1:1 for 4 h and secretion of granzyme A into the medium was determined by enzymatic assay (FIG. 4). Consistent with its effects in $^{51}$Cr-release assays, expression of 3A protein inhibited CTL activation. Wild-type poliovirus also inhibited CTL activation, although to a lesser degree than the 3A protein expressed from vaccinia.

Figure 2:
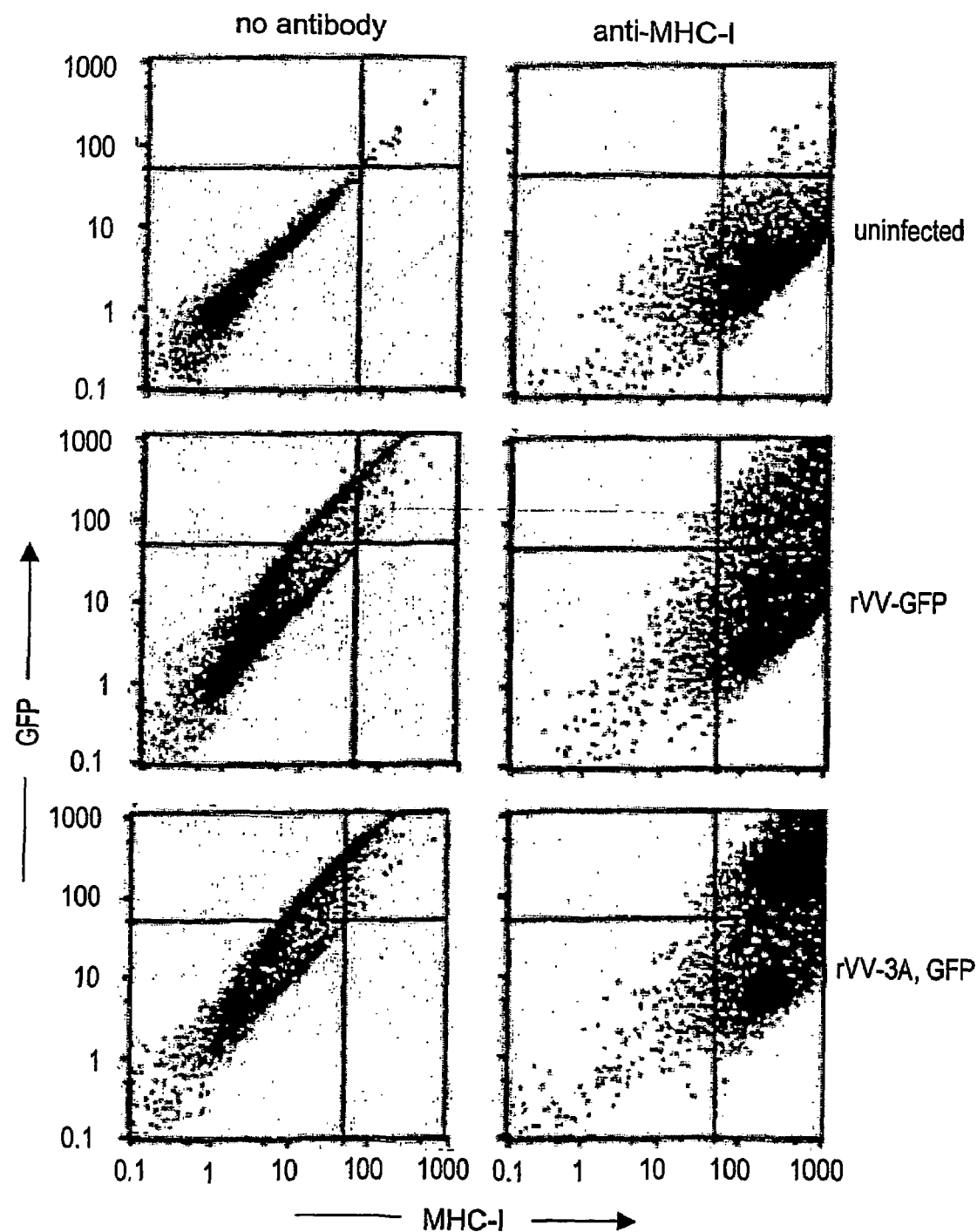
Figure 5:
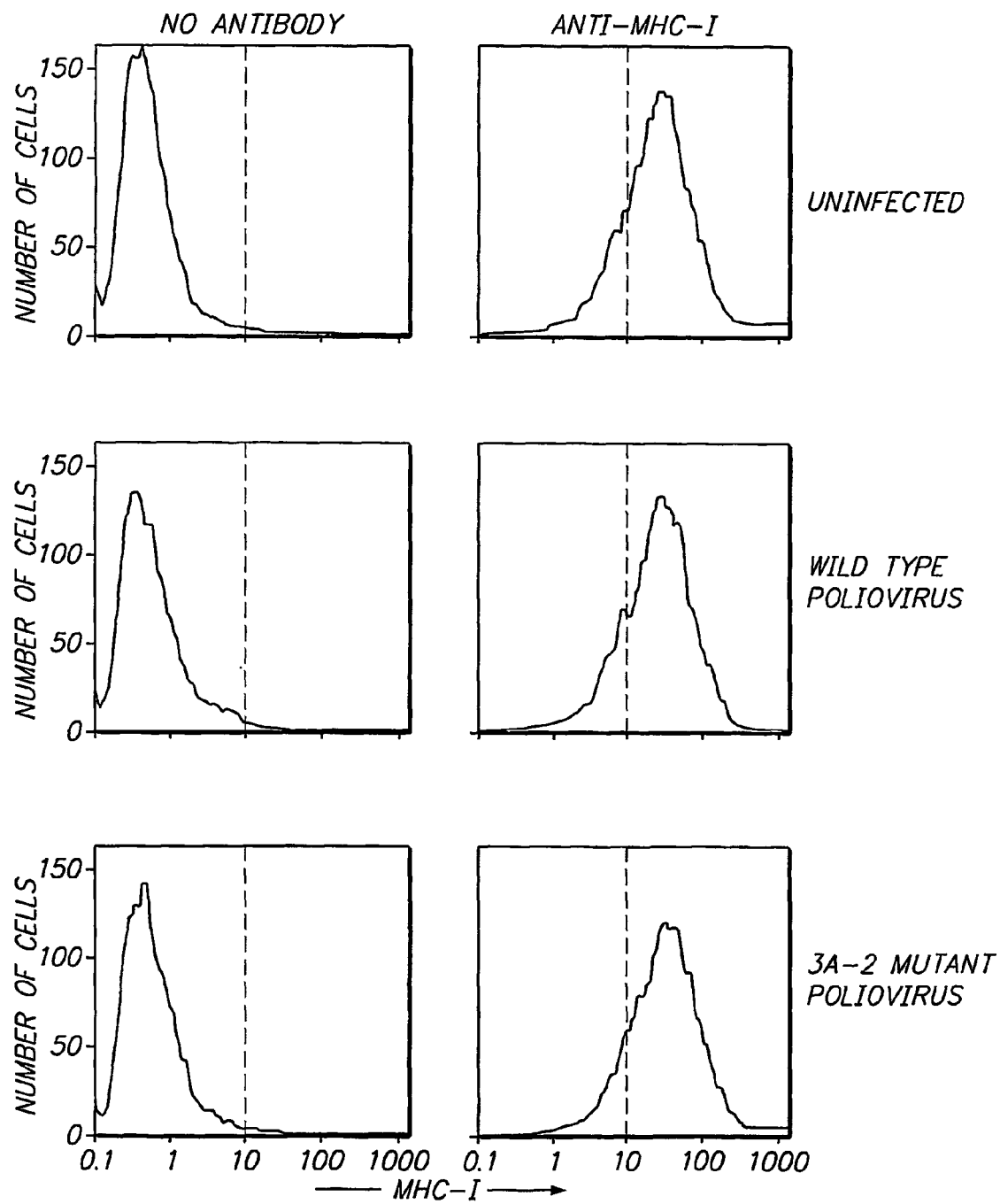

MHC I levels were analyzed in chimpanzee B lymphoblastoid cells were infected with either wild type poliovirus or 3A-2 mutant poliovirus. At 12 h post-infection, cells were stained with anti-MHC-I antibody and analyzed by FACS. As with 3A protein expression alone (FIG. 2), total MHC-I levels on the surface of the target cells were unaffected by poliovirus infection (FIG. 5).

To test the requirement of wild-type 3A function in the inhibition of antigen presentation by poliovirus, target cells were co-infected rVV-NS3/4 and a mutant poliovirus, 3A-2, that is cold-sensitive for RNA replication, but replicates normally at 37° C. in several lines of tissue-culture cells (Bernstein et al. (1988) *J. Virol.* 62:2922–2928) and in the target cells used here (data not shown). At all temperatures, the 3A-2 protein did not inhibit secretion as well as the wild-type 3A protein (Doedens et al. (1997) *J. Virol.* 71:9054–9064). Target cells infected with 3A-2 mutant poliovirus exhibited no inhibition of CTL activation (FIG. 4). This provides an example of the use of mutant 3A alleles in picornavirus vectors to increase the amount of antigen presentation in the context of MHC-I.

Example 5

Protein 3A Inhibits Secretion of Interferon-Beta, IL-6 and IL-8

Figure 6A:
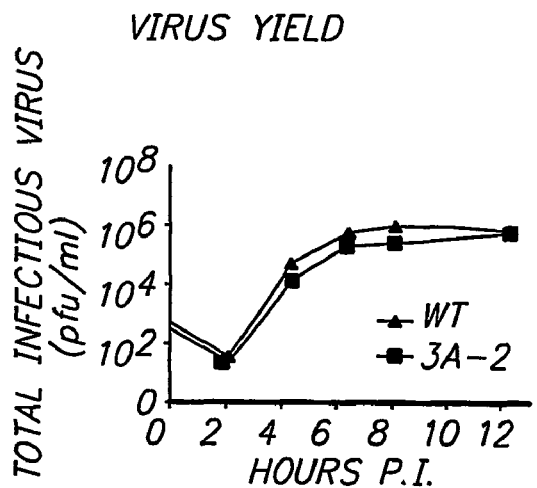

If the wild-type function of 3A protein serves to prevent the secretion of antiviral and pro-inflammatory cytokines during viral infection, infection of cells with a mutant poliovirus that does not inhibit protein secretion should cause the increased secretion of such cytokines. A mutant poliovirus, 3A-2, displays a cold-sensitive phenotype in some cell types, but grows normally at 37° C. (FIG. 6A; Bernstein et al, supra). The three-nucleotide insertion contained in this viral genome causes the addition of a Ser residue between amino acids 15 and 16 of 3A protein (FIG. 7, providing alignment of protein 3A amino acid sequences). The 3A-2 mutant protein, even when expressed to the same level as wild-type 3A protein, does not inhibit ER-to-Golgi traffic effectively (FIG. 6C; Doedens et al. (1995) *EMBO J* 14:894907). The existence of this mutant virus, and its ability to grow normally under some circumstances even though it is not as effective at inhibiting protein secretion, argues that the inhibition of ER-to-Golgi traffic is not required for poliovirus replication in tissue culture.

Figure 6B:
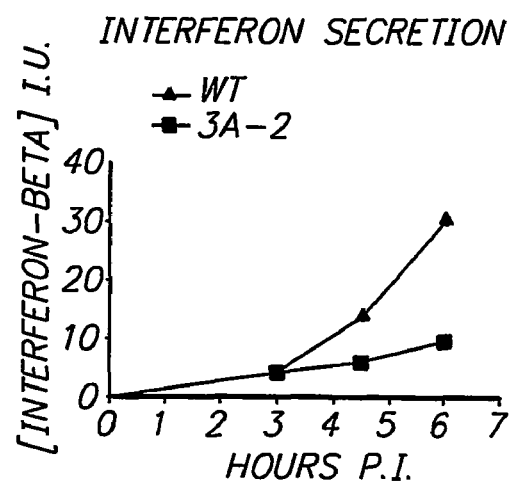
Figure 6C:
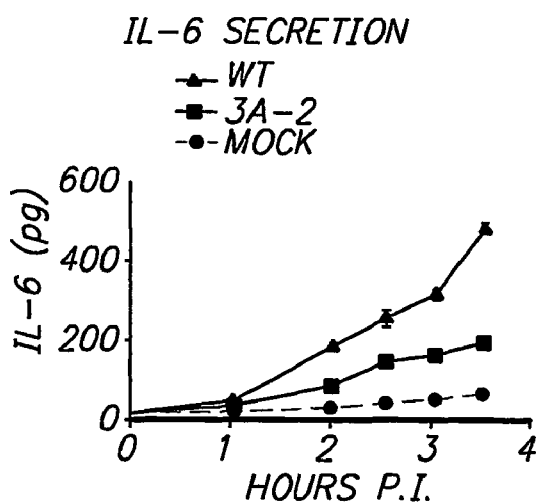
Figure 6D:
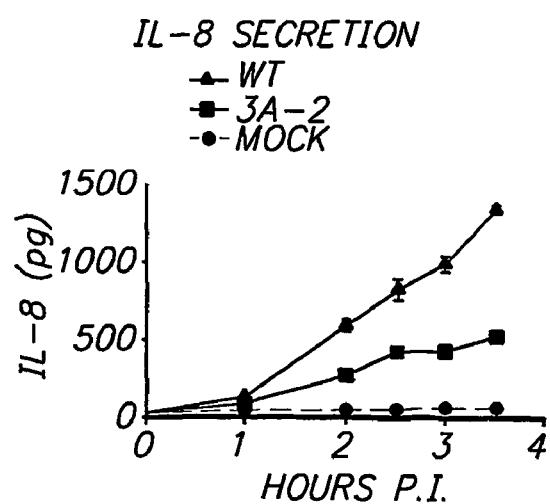

When human MG-63 cells were infected with wild-type and 3A-2 mutant poliovirus under identical conditions, higher amounts of cytokines interferon-β, IL6 (interleukin-6) and IL-8 (interleukin-8) were secreted from mutant-infected cells, as measured by quantitative ELISA (FIGS. 6B–6D). This did not result from significant differences in growth of the wild-type and 3A-2 mutant viruses (FIG. 6A) or from their abilities to inhibit host cell translation (data not shown). Therefore, in addition to decreasing antigen presentation on MHC I, wild-type 3A reduces the amount of functional antiviral cytokines secreted from infected cells.

Example 6

Identification of Variants of Protein 3A Having Activity in Inhibition of MHC I Antigen Presentation The ability of protein 3A, as well as the ability of candidate proteins having, for example, 3A wild-type activity in inhibition of the secretory pathway, or candidate proteins that lack or are reduced for such activity, can be assayed using a host cell line constructed to constitutively express a single-chain antibody derived from the pHook-2 vector (Stratagene, Carlsbad Calif.). This single-chain antibody recognizes a hapten, 4-ethoxymethylene-2-phenyl-2-oxazolin-5-one, abbreviated phOx (Hoogenboom et al. (1991) *Nucl. Acids Res.* 19:4133–4137). A signal peptide was fused to the N-terminus of the antibody-coding region, and a transmembrane domain fused to the C-terminus, allowing the antibody to be expressed at the cell surface (Chesnut et al (1996) *J. Imm. Methods* 193:17–27). A plasmid that encodes neomycin resistance as well as the coding sequences for the anti-phOx membrane-anchored antibody (αphOx), under the transcriptional control of a strong cytomegalovirus promoter and the translation control of the poliovirus IRES, was transfected into HeLa cells, neomycin resistant (neo$^R$) cell lines were cloned, and one cell line, HαphOx, was chosen on the basis of its high αphOx expression. For FACS analysis, cells can be stained with BSA conjugated to both phOx and fluorescein.

Figures 8A, 8B, 8C, 8D:
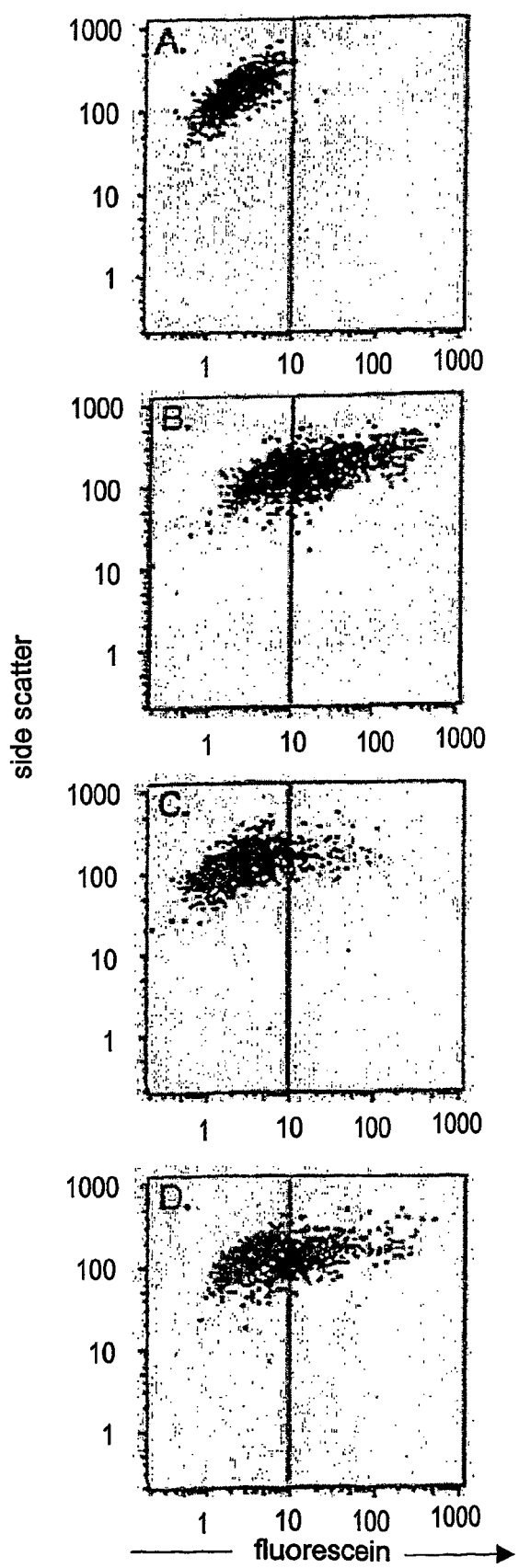

In the presence (FIG. 8B) but not the absence (FIG. 8A) of this staining reagent, approximately 50% of the HαphOx cells showed increased fluorescence by FACS analysis. When HαphOx cells were incubated with trypsin to remove the antibody, most of the increased fluorescence in the presence of the staining reagent disappeared (FIG. 8C). Then, after 3 hours of incubation at 37° C., new translation and secretion allowed much of the increased fluorescence signal to recover (FIG. 8D).

To isolate polioviruses that do not inhibit protein secretion (a Sec$^+$ phenotype), viruses are recovered from cells that show increased staining by the fluorescent phOx reagent after recovery from trypsin treatment In a first experiment, $10^7$ HαphOx cells were infected with poliovirus at a low multiplicity of infection, so that only 20% of the cells are infected, each with one virus to begin the infection. The high error rate of RNA-dependent RNA synthesis (Domingo et al. Ann. Rev. Microbiol. 51: 151–178) ensures that many mutations are present in these genomes. One hour post-infection, cells were treated with trypsin and allowed to recover for 3 h at 37° C. Translation of the αphOx antibody, because it is controlled by the poliovirus IRES, continues and is even trans-activated by poliovirus infection (Hambidge et al. (1992) Proc. Natl. Acad. Sci. USA 89:10272–10276). However, the inhibition of secretion by wild-type Sec$^-$ poliovirus should prevent most of the αphOx antibody from reaching the cell surface. Cells infected with any mutant, Sec$^+$ polioviruses should stain more intensely with the fluorescent phOx reagent.

After the first round of selection, viruses present in the most fluorescent cell population were recovered, titered and used to infect HαphOx cells for a second round For the first experiments, the fluorescent intensities used to gate the collected cells were varied more than will be done in the future; nevertheless, these gates were the same for the wild-type and cycled viruses in Rounds 3 and 4, allowing direct comparisons to be made.

TABLE 1

| Cycle | Virus | % cells | PFU/cell | Increase |
|---|---|---|---|---|
| 1 | WT | 0.15 | 0.002 | — |
| 2 | WT | | | |
| | P2 | 3.8 | 1.6 | — |
| 3 | WT | 3.7 | 0.28 | |
| | P3 | 2.3 | 0.36 | 1 |
| 4 | WT | 1.1 | 0.024 | |
| | P4 | 1.4 | 0.468 | 20 |

As illustrated in Table 1, in cycle 1, the most fluorescent 0.15% of the cell population was recovered, virus extracted, and used to infect cells for cycle 2. From cycle 2, the 3.8% most fluorescent cells were isolated, virus extracted, and used to infect cells for cycle 3. For cycles 3 and 4, the yield of virus form cells infected with both wild-type (WT) and pooled, cycled viruses was determined (P3: cycle 3 viruses; P4: cycle 4 viruses).

As a first screen to determine whether individual viruses present in Round 4 (Table 1) were Sec$^+$, an assay based on the increased secretion of IL-8 during infection with 3A-2 mutant virus (as performed above) was used Forty individual plaques were isolated and used to infect monolayers of MG-63 cells in 96-well microtiter dishes at multiplicities of infection greater than 10 plaque-forming units/cell. After 5 hr. infection, the supernatants were assayed for the presence of IL-8, which should be highest in wells infected with Sec$^+$ viruses that do not effectively inhibit protein secretion. Of the eight virus isolates that appeared Sec$^+$, six have withstood subsequent testing with carefully matched multiplicities of infection (MOIs); two of these isolates allow the accumulation of four-fold more IL-8 than wild-type poliovirus, an even stronger Sec$^+$ phenotype than that displayed by 3A-2 virus in the same experiment (data not shown). Therefore, this selection scheme can be used to isolate poliovirus variants that grow well in tissue-culture cells but display a reduced ability to inhibit host protein secretion.

Selections such as that described above will be repeated in several pools, to avoid the isolation and characterization of sibling viruses. Two Sec$^+$ viruses from the selection shown in Table 1, and new isolates from subsequent selections, will be tested individually for their ability to inhibit modification of VSV-G (Doedens et a. (1995) EMBO J 14:894–907) and to display robust growth phenotypes in tissue culture. The 3A alleles will be amplified and sequenced from several candidate Sec$^+$ viruses to characterize any mutations they contain. Mutations of interest will be recloned into a full-length poliovirus cDNA, infectious RNA will be transcribed in vitro using T7 RNA polymerase, and viruses will be obtained by RNA transfection as described (Diamond et al. (1994) J. Virol. 68:863–876; Hope et al. (1997) J. Virol. 71:9490–9498). This assay can be screened to select for viruses and expression vectors that either increase or decrease the rate of cellular protein secretion.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A recombinant viral vector comprising:
   a first nucleic acid comprising a sequence encoding an exogenous polypeptide for expression in a host cell;
   a second nucleic acid comprising a sequence encoding a picornaviral protein 3A for expression in the host cell, wherein the picornaviral 3A protein is selected from a poliovirus 3A protein, a coxsackievirus B3 protein, and a rhinovirus 14 protein;

wherein the viral vector is a recombinant retroviral vector, a recombinant adenoviral vector, a recombinant alphavirus vector, a recombinant adeno-associated viral vector, or a recombinant poxvirus vector and wherein expression of the recombinant picornaviral protein 3A results in inhibition of presentation of the exogenous polypeptide on an MHC class I molecule of the host cell.

2. The recombinant viral vector of claim 1, wherein the exogenous polypeptide is an antigen.

3. The recombinant viral vector of claim 2, wherein the antigen elicits a humoral immune response in a host.

4. The recombinant viral vector of claim 1, wherein the picornaviral protein 3A is a polioviral protein 3A.

5. A recombinant picornaviral vector comprising:

a first sequence encoding an exogenous polypeptide for expression in a host cell; and at least a portion of a picornaviral genome, wherein the picornaviral genome encodes a mutant 3A protein with reduced ability to inhibit host cell protein secretion, wherein the mutant picornaviral 3A protein is selected from a mutant poliovirus 3A protein, a mutant coxsackievirus B3 protein, and a mutant rhinovirus 14 protein.

6. The recombinant picornaviral vector of claim 5, wherein the exogenous polypeptide is an antigen.

7. The recombinant picornaviral vector of claim 6, wherein the antigen elicits an antigen-specific cellular immune response.

8. The recombinant picornaviral vector of claim 5, wherein the picornaviral genome is a polioviral genome.

9. A method of enhancing an antigen-specific cellular immune response in a host, the method comprising:

delivering to a mammalian cell in the host the picornaviral vector of claim 5, wherein expression of the exogenous polypeptide and the mutant 3A protein in the mammalian cell result in presentation of an antigenic peptide of the exogenous polypeptide on MHC class l, and enhancement of a cellular immune response in the host specific for the exogenous polypeptide.

10. The method of claim 9, wherein the picornaviral vector comprises a polioviral genome.

11. The vector of claim 6, wherein the antigen is an antigen of an intracellular pathogen.

12. The vector of claim 6, wherein the antigen is a tumor antigen.

13. An immunogenic composition comprising the vector of claim 5 and a pharmaceutically acceptable excipient.

14. The method of claim 9, wherein the exogenous polypeptide is an antigen.

15. The method of claim 14, wherein the antigen is an antigen of an intracellular pathogen.

16. The method of claim 14, wherein the antigen is a tumor antigen.

* * * * *

UNITED STATES PATENT AND TRADEMARK OFFICE
CERTIFICATE OF CORRECTION

PATENT NO. : 7,247,619 B2
APPLICATION NO. : 10/276752
DATED : July 24, 2007
INVENTOR(S) : Karla Kirkegaard et al.

It is certified that error appears in the above-identified patent and that said Letters Patent is hereby corrected as shown below:

On the Title page Item 73

- Please add: The Board of Trustees of the Leland Stanford Junior University, Palo Alto, California Signed and Sealed this Twenty-fifth Day of December, 2007

JON W. DUDAS
*Director of the United States Patent and Trademark Office*